United States Patent [19]
Marhold

[11] Patent Number: 5,489,715
[45] Date of Patent: Feb. 6, 1996

[54] PROCESS FOR PREPARING 4,5-DIFLUOROBENZALDEHYDES

[75] Inventor: Albrecht Marhold, Leverkusen, Germany

[73] Assignee: Bayer Aktiengesellschaft, Leverkusen, Germany

[21] Appl. No.: 334,716

[22] Filed: Nov. 4, 1994

[30] Foreign Application Priority Data

Nov. 11, 1993 [DE] Germany .......................... 43 38 525.7

[51] Int. Cl.[6] .................................................. C07C 45/63
[52] U.S. Cl. ......................... 568/437; 568/425; 568/426
[58] Field of Search ................................... 568/425, 426, 568/437

[56] References Cited

U.S. PATENT DOCUMENTS 5,072,038  12/1991  Klauke et al. .

FOREIGN PATENT DOCUMENTS 0289942  11/1988  European Pat. Off. .
3420796  12/1985  Germany .

*Primary Examiner*—Werren B. Lone
*Attorney, Agent, or Firm*—Sprung Horn Kramer & Woods

[57] ABSTRACT

4,5-Difluorobenzaldehydes of a given formula are prepared by the reaction of corresponding benzaldehydes with a fluorinating agent.

7 Claims, No Drawings

PROCESS FOR PREPARING 4,5-DIFLUOROBENZALDEHYDES

BACKGROUND OF THE INVENTION

The present invention relates to a process for preparing ring-fluorinated benzaldehydes containing fluorine atoms in the 4 and 5 positions relative to the aldehyde group.

EP-B1-289 942 discloses that in chlorinated, brominated and/or iodated benzaldehydes, the halogen atoms can be completely or partially replaced by fluorine. Examination of the examples of this patent specification shows that, using this process, only chlorine atoms which are in the 2 and 4 positions relative to the aldehyde group can be replaced by fluorine (see Examples 1 to 18). Chlorine atoms in the 3 and/or 5 position relative to the aldehyde group remain unchanged (see Example 19). Thus, if 3-and/or 5-fluorobenzaldehydes are to be prepared, a fundamentally different synthetic route has to be sought.

Furthermore, EP-B1-289 942 shows that, in the manner described there, 2,4-dichlorobenzaldehydes can be converted only into 2,4-difluorobenzaldehydes, but not into 2-chloro-4-fluorobenzaldehydes or 2-fluoro-4-chlorobenzaldehydes (Example 16).

SUMMARY OF THE INVENTION

A process has now been found for preparing 4,5-difluorobenzaldehydes of the formula (I)

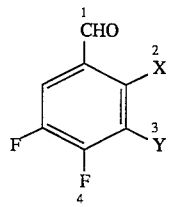

(I)

in which
X represents fluorine or chlorine and
Y represents hydrogen or chlorine,
which is characterized in that benzaldehydes of the formula (II)

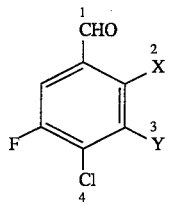

(II)

in which X and Y are as defined for formula (I), are reacted with a fluorinating agent.

DETAILED DESCRIPTION OF THE INVENTION

Suitable starting materials for the process of the invention are, for example, 2,5-difluoro-4-chlorobenzaldehyde, 5-fluoro-2,4-chlorobenzaldehyde, 3,5-di-fluoro-3,4-dichlorobenzaldehyde and 5-fluoro-2,3,4-trichlorobenzaldehyde.

Suitable fluorinating agents are, for example, sodium, potassium and/or caesiumfluoride. Preference is given to potassium fluoride and a mixture of sodium fluoride and potassium fluoride and also a mixture of sodium fluoride and caesium fluoride.

From 0.8 to 2 mol of fluorinating agent can, for example, be used per 1 mol of chlorine to be replaced in the benzaldehyde of the formula (II) used. This amount is preferably from 1 to 1.5 mol.

It is generally advantageous to carry out the fluorination of the invention in the presence of a solvent. Suitable solvents are, for example: dimethylacetamide, diethylacetamide, dibutylacetamide, N-methylpyrrolidone, N-methylcaprolactam, dimethyl sulphoxide, dimethyl sulphone and tetramethylene sulphone.

Preference is given to dimethylacetamide, N-methylpyrrolidone and tetramethylene sulphone.

From 50 to 200 ml of a solvent can, for example, be used per 1 mol of fluorinating agent used. It is also possible to use mixtures of various solvents.

It is generally also advantageous to carry out the fluorination of the invention in the presence of a catalyst. Suitable catalysts are, for example: crown ethers and quaternary ammonium and phosphonium halides.

Preference is given to crown ethers and phosphonium halides.

From 0.01 to 0.1 tool of catalyst can, for example, be added per 1 tool of benzaldehyde of the formula (II) used. This amount is preferably from 0.01 to 0.05 mol.

The fluorination of the invention can be carried out, for example, at temperatures of from 160° to 230° C. Preference is given to from 180° to 210° C.

The pressure can be, for example, from 1 to 20 bar during the reaction. Preference is given to from 1 to 6 bar.

The process of the invention can be carried out batch-wise and continuously.

The reaction mixture present after carrying out the process of the invention can be worked up, for example, by separating off the reaction products by distillation.

It is generally advantageous in carrying out the process of the invention to first charge the fluorinating agent and the solvent and then, optionally in vacuo, to distil off a small amount of solvent together with any water present and to only then add the benzaldehyde of the formula (II) and optionally a catalyst and/or an inert gas (e.g. $N_2$).

Benzaldehydes of the formula (II) which can be used in the process of the invention can be prepared, for example, from the corresponding 3-amino-4-chlorotoluene or 5-amino-2,4-dichlorotoluene. These can be converted into the corresponding 3-fluoro-chlorotoluene by reaction with sodium nitrite and dimethylamine and subsequent boiling down in the presence of fluoride ions (for reaction principle, see U.S. Pat. No. 4,075,252).

From this fluorochlorotoluene, the corresponding benzaldehyde of the formula (II) can be obtained by chlorination of the methyl group and subsequent acid saponification (for reaction principle, see Houben-Weyl, Methoden der organischen Chemie, 4th edition, Volume VII/1, p. 211 ff.)

This route to the benzaldehydes of the formula (II) required is illustrated, as an example, by the following reaction scheme:

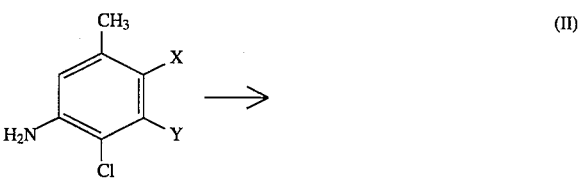

(II)

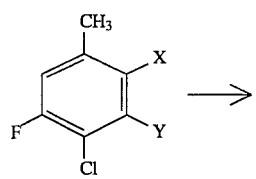

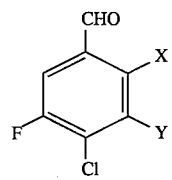

The 3-amino-4-chlorotoluenes required as starting materials in this case are commercial products or can be obtained by ring-chlorination from known acid halides via a Rosenmund reaction.

The ring-fluorinated benzaldehydes of the formula (I) which can be prepared by the process of the invention are important intermediates for the preparation of medicaments.

For example, it is possible to prepare antibacterial agents from the ring-fluorinated benzaldehydes of the formula (I) by first converting them into the corresponding benzoyl chloride by chlorination at the aldehyde group. This benzoyl chloride can then be converted into an antibacterial agent as described in EP-A1-550 903.

In the light of the prior art indicated in the introduction, it is extremely surprising that, in a 3-fluoro- 4-chlorobenzaldehyde, the chlorine can be successfully replaced by fluorine according to the invention. Furthermore, it is surprising that, depending on the selected amount of the fluorinating agent, any chlorine atom located in the 2 position relative to the aldehyde group can optionally be replaced by fluorine or can be left unchanged. This stepwise selectivity of the fluorination could in no way be foreseen, since both chlorine atoms (i.e. those located in the 2 and 4 positions) are located in activated positions.

EXAMPLES

EXAMPLE 1

163 g of potassium fluoride in 500 ml of tetramethylene sulphone were placed in a stirred apparatus and partially distilled in vacuo (distillate: 100 ml). 142 g of 2,3,4-trichloro-5-fluorobenzaldehyde were then added and after stirring for 10 hours under nitrogen at 190° C., the product was, with reduction of the pressure down to 20 mbar, distilled off into a cooled reservoir (120 g of distillate). The new distillation gave 65 g of 3-chloro- 2,4,5-trifluorobenzaldehyde (boiling point: from 66° to 68° C./15 mbar) and, in the subsequent fraction, 2,3 -di-chloro-4,5-difluorobenzaldehyde which can be used again in the fluorination.

EXAMPLE 2

87 g of potassium fluoride in 225 ml of tetramethylene sulphone were placed in a stirred apparatus and partially distilled at 20 mbar for the purpose of drying. 96.5 g of 2,4-dichloro-5-fluorobenzaldehyde and 5 g of tetraphenylphosphonium bromide were then added and the mixture was heated for 5 hours at 190° C. while stirring. The reaction mixture was subsequently distilled at 20 mbar. This gave 68 g of distillate containing 78% by weight of 2,4,5-trifluorobenzaldehyde and 9.4% by weight of 2-chloro-4,5-difluorobenzaldehyde. Fraction distillation gave 51.5 g of 2,4,5-trifluorobenzaldehyde having a boiling point of from 65° to 67° C./20 mbar and 51.2 g of 2-chloro-4,5-difluorobenzaldehyde having a boiling point of from 90 to 92° C./20 mbar.

EXAMPLE 3

The procedure of Example 2 was repeated, but no tetraphenylphosphoniumbromide was added and the reaction time was increased to 10 hours. This gave 78 g of crude distillate, containing 22.2% by weight of 2,4,5-trifluorobenzaldehyde and 49.4% by weight of 2-chloro- 4,5-difluorobenzaldehyde.

EXAMPLE 4

Preparation of starting material a) 358 g of 3-amino-4,6-dichlorotoluene were added dropwise to a mixture of 400 ml of 35% strength by weight aqueous hydrochloric acid and 1150 ml of water. The mixture was stirred for 1 hour at 50° C. and then cooled to 0° C. 168 g of sodium nitrite dissolved in 320 ml of water were then quickly metered in between 0° and 5° C. and, after the addition, the mixture was stirred for a further 30 minutes.

b) In the meantime, 2200 ml of water and 264 g of 40% strength aqueous dimethylamine solution were placed in another reaction vessel, 641 g of sodium carbonate were dissolved therein and 920 ml of chloroform were added. Subsequently, the diazonium salt solution obtained as described in a) was metered in at 5° C. and, after the addition was complete, the mixture was stirred further for 5 hours. The phases were subsequently separated, the organic phase was washed twice with water and, after drawing off the solvent at reduced pressure, gave 420 g of crude 3-dimethyltriazenyl-4,6-dichlorotoluene having a melting point of from 38° to 40° C., which product was used in the next reaction stage without further purification.

c) 720 ml of anhydrous hydrogen fluoride were placed in a stainless-steel pressure vessel and the triazene compound obtained as described in b) was metered in at −6° C. The vessel was subsequently pressurized with 8 bar of nitrogen and heated while stirring. At from 130° to 140° C., the pressure was adjusted to 20 bar using a pressure-maintenance valve. After the reaction was complete (no further nitrogen evolution), the mixture was cooled and the hydrogen fluoride still present was distilled off. The remaining residue was dissolved in dichloromethane, the solution was washed with water and the solvent was subsequently removed in vacuo. The residue then remaining was distilled to give 397 g of 3-fluoro-4,6-dichlorotoluene having a boiling point of 75° C./15 mbar.

d) 537 g of the product from c) were placed at 120° C. in a chlorination apparatus made of glass and irradiated with an UV lamp. Elemental chlorine was then passed in at the rate at which it was absorbed. As soon as the reaction mixture had a refractive index of $n_D^{20}$ of 1.5500, the passing in of chlorine was stopped. The reaction mixture was blown out with nitrogen and distilled via a 60 cm packed column. This gave 340 g of 3-fluoro-4,6-dichlorobenzal chloride having a boiling point of from 125 to 126° C./20 mbar. The first fraction was able to be used again in this chlorination.

e) 600 ml of 95% strength by weight sulphuric acid were placed at 40° C. in a stirred apparatus and 266 g of the benzal chloride obtained as described in d) were metered in. The mixture was stirred further until gas evolution had ended. The mixture was then poured onto 1 kg of ice and the product was taken up in dichloromethane. Distillation of the organic phase gave 155 g of 3-fluoro-4,6-dichlorobenzaldehyde having a boiling point of from 110° to 112° C./20 mbar.

EXAMPLE 5

Another route to a starting material of the formula (II)

A hydrogenation apparatus was charged with 800 ml of dry toluene and 250 g of 2,3,4-trichloro-5-fluorobenzoyl chloride together with 40 g of a catalyst containing 5% by weight of metallic palladium on a barium sulphate support. Hydrogen was then passed in at from 40° to 80° C. The progress of the hydrogenation was monitored by means of gas chromatography and was stopped after the quantitative consumption of the benzoyl chloride used. After filtration of the reaction mixture, the solution was freed of toluene by distillation and the residue was recrystallized from 223 g of cyclohexane. This gave 148 g of 2,3,4-trichloro-5-fluorobenzaldehyde having a melting point of from 78° to 79° C.

EXAMPLE 6

Reaction of a ring-fluorinated benzaldehyde of the formula (I) to give the corresponding benzoyl chloride 100 ml of 2-chlorobenzotrifluoride and 4.5 g of potassium chloride were placed at 110° C. in a chlorination apparatus with UV irradiation and 50 g of 3-chloro-2,4,5-trifluorobenzaldehyde in 50 ml of 2-chlorobenzotrifluoride were subsequently added dropwise with exclusion of air. After addition of 10 ml of the solution, chlorine was added at the rate at which it was absorbed. The metered addition was continued until the entire amount of the aldehyde used had reacted (gas chromatographic monitoring). Distillation of the reaction mixture gave 52 g of 3-chloro-2,4,5-trifluorobenzoyl chloride having a boiling point of 92° C./20 mbar.

Use of 2,4,5-trifluorobenzaldehyde in place of 3-chloro-2,4,5-trifluorobenzaldehyde gave 2,4,5-trifluorobenzoyl chloride in a completely analogous manner.

What is claimed is:

1. A process for preparing a 4,5-difluorobenzaldehyde of the formula (I)

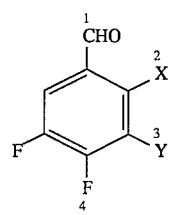

in which
X represents fluorine or chlorine and
Y represents hydrogen or chlorine,
wherein a benzaldehyde of the formula (II)

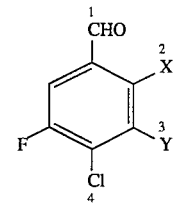

in which X and Y are as defined for formula (I), is reacted with one or more fluorinating agents selected from the group consisting of sodium fluoride, potassium fluoride and cesium fluoride.

2. The process of claim 1, wherein the fluorinating agent is used in an amount of from 0.8 to 2 mol per 1 mol of chlorine to be replaced in the benzaldehyde used.

3. The process of claim 1, which is carried out in the presence of a solvent.

4. The process of claim 1, which is carried out in the presence of a catalyst.

5. The process of claim 1, which is carried out at temperatures in the range from 160° to 230° C.

6. The process of claim 1, wherein the benzaldehyde of the formula (II) used is that which is obtainable from the corresponding 3-amino-4-chlorotoluene or the corresponding 5-amino-2,4-dichlorotoluene by reaction with sodium nitrite and dimethylamine and subsequent boiling down in the presence of fluoride ions, and chlorination and acid saponification of the fluorochlorotoluene obtainable in this way.

7. In a process for the preparation of an antibacterial agent by (i) chlorinating a difluorobenzaldehyde at the aldehyde group to obtain the corresponding benzoyl chloride, and (ii) converting the benzoyl chloride into the antibacterial agent, the improvement wherein the 4,5-difluorobenzaldehyde of claim 1 is used as said difluorobenzaldehyde.

* * * * *